United States Patent [19]

Toussant et al.

[11] Patent Number: 4,681,579
[45] Date of Patent: Jul. 21, 1987

[54] ABSORBENT ARTICLE HAVING RESERVOIRS

[75] Inventors: John W. Toussant; Ted L. Blaney, both of West Chester, Ohio

[73] Assignee: The Procter & Gamble Co., Cincinnati, Ohio

[21] Appl. No.: 786,900

[22] Filed: Oct. 11, 1985

[51] Int. Cl.[4] ............................................. A61F 13/16
[52] U.S. Cl. ................................................ 604/385 R
[58] Field of Search ................. 604/385.1, 385.2, 393, 604/394, 397, 398

[56] References Cited

U.S. PATENT DOCUMENTS

| | | |
|---|---|---|
| 3,530,859 | 9/1970 | Helmowitz . |
| 3,729,005 | 4/1973 | Lee et al. . |
| 3,744,494 | 7/1973 | Marsan . |
| 3,860,003 | 1/1975 | Buell . |
| 3,863,637 | 2/1975 | MacDonald et al. . |
| 3,929,134 | 12/1975 | Karami . |
| 4,210,143 | 7/1980 | DeJonckheere . |
| 4,246,900 | 1/1981 | Schröder . |

Primary Examiner—John D. Yasko
Attorney, Agent, or Firm—Steven W. Miller; John M. Pollaro; Richard C. Witte

[57] ABSTRACT

A disposable absorbent article such as a diaper with a liquid pervious topsheet, a liquid impervious backsheet, an absorbent core disposed between the topsheet and the backsheet, flexible side flaps extending outwardly from and along each side edge of the absorbent core in at least the crotch region of the diaper, elastic members secured to the side flaps, and a reservoir. The reservoir collects and holds body exudates, especially loose fecal material, until the diaper is removed. Leakage prevention is enhanced because body exudates would have to flow not only above and over the reservoir but also beyond the elasticized side flaps; leakage being additionally prevented by the elasticized side flaps because they form an additional liquid impervious barrier about the body of the wearer.

5 Claims, 5 Drawing Figures

ABSORBENT ARTICLE HAVING RESERVOIRS

FIELD OF THE INVENTION

The present invention relates to absorbent articles such as disposable diapers, and more particularly, to absorbent articles having a reservoir which improves the containment characteristics of the article, especially the containment of loose fecal material.

BACKGROUND OF THE INVENTION

The major function of absorbent articles such as disposable diapers and adult incontinent briefs is to absorb and contain body exudates. Such articles ae intended to prevent body exudates from soiling, wetting, or otherwise contaminating clothing or other articles, such as bedding, that come in contact with the wearer. The most common modes of failure for such products occur when body exudates leak from the edges of the article to adjacent clothing or are not immediately absorbed within the absorbent article and leak out of the gaps between the absorbent article and the wearer's leg or waist to adjacent clothing. This is most evident with loose fecal material which is not easily absorbed by the absorbent article and tends to "float" on the top surface of the absorbent article.

Contemporary disposable diapers, such as those disclosed in U.S. Pat. No. 3,860,003 issued to Kenneth Barclay Buell on Jan. 14, 1975, have a topsheet, a backsheet, an absorbent core and elasticizied leg flaps to improve both wearing comfort and the ability to contain body exudates. These elasticized leg flaps prove effective generally to prevent wicking and overflow from a fluid laden absorbent article to clothing contacting the edges of the article in that the elasticized leg flaps present a fluid impervious barrier between the edge of the absorbent core and the contacting clothing, and in addition, provide a gasketing action about the legs of the wearer. Despite the effectiveness of such structures, however, body exudates, especially loose fecal material, can leak through the elasticized leg flaps and soil the wearer's clothing because the diaper does not constrain the free flow of such material nor provide a structure to hold it within the diaper so that as such material freely floats on the top surface of the topsheet, it tends to work its way past the elasticized leg flaps.

Therefore, it is an object of the present invention to provide an absorbent article which has improved containment characteristics.

It is an additional object of the present invention to provide an absorbent article having a reservoir which acts as a restraint against the leakage of body exudates.

It is a further object of the present invention to provide an absorbent article having elasticized side flaps and reservoirs so as to provide a dual restraint against the lateral flow of body exudates, thereby improving the containment characteristics of the absorbent article, especially in regard to loose fecal material.

It is also an object of the present invention to provide an absorbent article having increased comfort for the wearer and a better initial fit on the wearer.

These and other objects of the invention will be more readily apparent when considered in reference to the following description and when taken in conjunction with the accompanying drawings.

SUMMARY OF THE INVENTION

In accordance with the present invention, a disposable absorbent article such as a diaper is provided with a liquid previous topsheet, a liquid impervious backsheet, an absorbent core disposed between the topsheet and the backsheet, flexible side flaps extending outwardly from and along each side edge of the absorbent core in at least the crotch region of the diaper, elastic members secured to the side flaps, and a reservoir. The reservoir collects and holds body exudates, especially loose fecal material, until the diaper is removed. Leakage prevention is enhanced because body exudates would have to flow not only above and over the reservoir but also beyond the elasticized side flaps; leakage being additionally prevented by the elasticized side flaps because they form an additional liquid impervious barrier about the body of the wearer.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

DETAILED DESCRIPTION OF THE INVENTION

Figure 1:
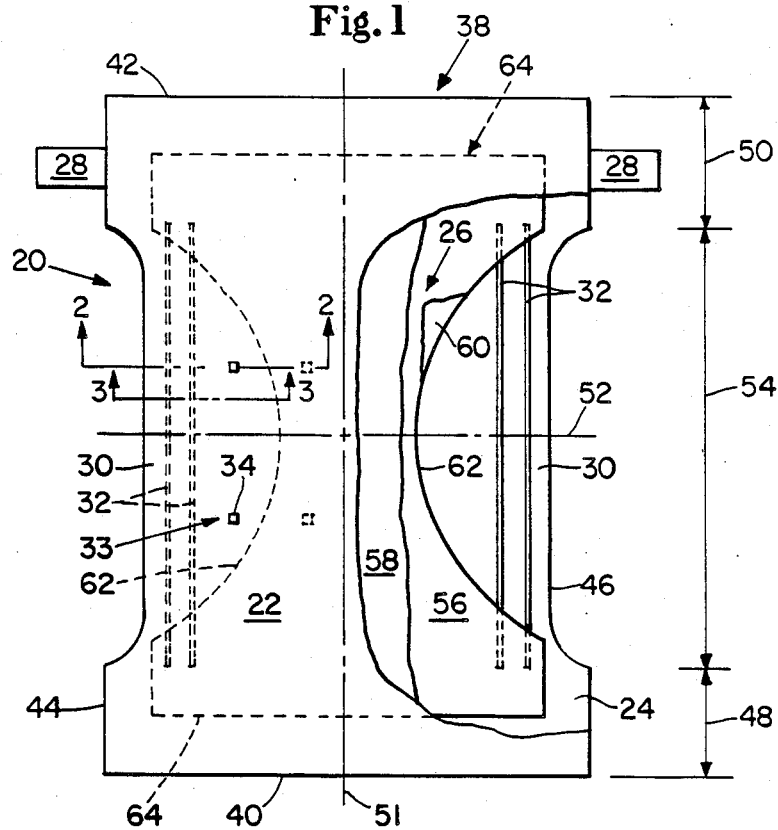
FIG. 1 is a plan view of a disposable diaper embodiment of the present invention having portions cut away to reveal its underlying structure.

As used herein, the term "disposable absorbent article" refers to articles which absorb and contain body exudates and more specifically refers to articles which are placed against or in proximity to the body of the wearer to absorb and contain the various exudates discharged from the body, and to articles which are intended to be discarded after a single use (i.e., they are not intended to be laundered or otherwise restored or reused). A preferred embodiment of the disposable absorbent article of the present invention, diaper 20, is shown in FIG. 1. As used herein, the term "diaper" refers to a garment generally worn by infants and incontinent persons, which is worn about the lower torso of the wearer. It should be understood, however, that the present invention is also applicable for use in other disposable absorbent articles such as incontinent briefs and the like.

FIG. 1 is a plan view of the diaper 20 of the present invention in the flat-out, uncontracted state (i.e., with all elastic induced contraction pulled out and prior to any folding operation performed on the article) with portions of the structure torn away to more clearly show the construction of the diaper 20 and with the portion of the diaper which contacts the wearer facing the viewer. The diaper 20 comprises a liquid pervious topsheet 22; a liquid impervious backsheet 24, an absorbent core 26 disposed between the topsheet 22 and the backsheet 24; a pair of tape-tab fasteners 28; flexible side flaps 30; elastic members 32 secured to the side flaps 30; securing means 33 such as glue spots 34 for securing length portions of the side flaps 30 to the topsheet 22 so as to form a reservoir 36 (not shown in FIG. 1) that contains and holds body exudates. While the liquid pervious topsheet 22, absorbent core 26, liquid impervious backsheet 24, flexible side flaps 30 and elastic members 32 may be assembled in a variety of well known configurations, a preferred diaper configuration is described generally in U.S. Pat. No. 3,860,003 entitled "Contractible Side Portions for Disposable Diaper", which issued to K. B. Buell on Jan. 14, 1975, and which patent is incorporated herein by reference.

FIG. 1 shows a preferred embodiment of the diaper 20 in which the topsheet 22 and the backsheet 24 are coextensive and have length and width dimension generally larger than those of the absorbent core 26. The topsheet 22 is superposed on the backsheet 24 thereby forming a periphery 38 of the diaper 20. The periphery 38 defines the outer periphery or, in other words, the outer edges of the diaper 20. The periphery 38 comprises end edges 40 and 42, and longitudinal edges 44 and 46.

The diaper 20 has waist regions 48 and 50 extending, respectively, from the end edges 40 and 42, of the diaper periphery 38 toward the lateral centerline 52 of the diaper 20 a distance of from about $\frac{1}{4}$ to about $\frac{1}{3}$ the length of diaper 20. The waist regions 48 and 50 comprise those portions of the diaper 20 which, when worn, is positioned between the legs of the wearer and covers the lower torso of the wearer.

Figure 2:
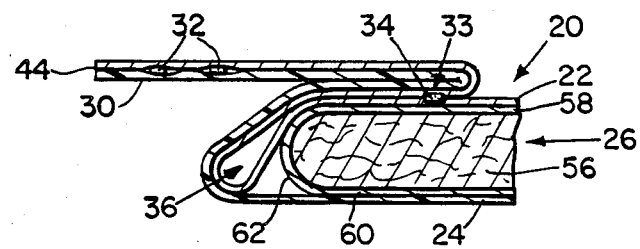
FIG. 2 is an enlarged scale, fragmentary sectional view taken along section line 2—2 of FIG. 1.

FIG. 2 is a fragmentary sectional view of the diaper 20 taken along line 2—2 of FIG. 1, and shows the diaper 20 in condition to be placed on the wearer. The absorbent core 26 comprises an absorbent layer 56 and first and second tissue layers 58 and 60, respectively, that envelope the absorbent layer 58. The absorbent core 26 is disposed between the topsheet 22 and the backsheet 24; both the topsheet 22 and the backsheet 24 extending beyond the side edge 62 of the absorbent core to define the side flap 30. The topsheet 22 and the backsheet 24 also enclose the flap elastic members 32 in the side flap 30 adjacent the longitudinal edge 46 of the diaper 20. As shown in FIG. 2, the side flap 30 is folded inwardly toward the longitudinal centerline 51 of the diaper 20 along a longitudinal fold line located inwardly from the longitudinal edge 46 to define a first fold. The respective longitudinal edge 46 is further folded outwardly from the longitudinal centerline 51 along a second longitudinal fold line to define a second longitudinal fold overlying the first fold. This folding generally being designated as a C-fold. The first fold is secured to the topsheet 22 by the securing means 33 shown as glue spots 34. This folding and securing of the side flaps 30 forms the reservoir 36 along the side edge 62 of the absorbent core 26. While the reservoir is shown in FIG. 2 as being closed to the inflow of exudates by the securing means 33, the reservoir 36 is still capable of retaining and holding exudates until the diaper 20 can be removed.

Figure 3:
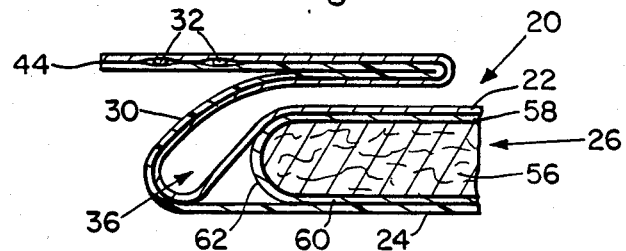
FIG. 3 is an enlarged scale, fragmentary sectional view taken along section line 3—3 of FIG. 1.

FIG. 3 is a fragmentary sectional view of the diaper 20 taken along line 3—3 of FIG. 3. The construction of the diaper 20 in this region is identical to the construction shown in FIG. 2 except that the first fold is not secured to the topsheet 22. Thus, the reservoir is shown as standing open (i.e., ready to collect, contain and hold unabsorbed exudates).

The topsheet 22 is compliant, soft feeling, and non-irritating to the wearer's skin. Further, the topsheet 22 is liquid pervious permitting liquids to readily penetrate through its thickness. A suitable topsheet may be manufactured from a wide range of materials, such as porous foams, reticulated foams, apertured plastic films, natural fibers (e.g., wood or cotton fibers), synthetic fibers (e.g., polyester or polypropylene fibers) or from a combination of natural and synthetic fibers. Preferably, it is made of a hydrophobic material to isolate the wearer's skin from fluids in the absorbent core 26.

A particularly preferred topsheet 22 comprises staple length polypropylene fibers having a denier of about 1.5, such as Hercules Type 151 polypropylene marketed by Hercules, Inc., of Wilmington, Del. As used herein, the term "staple length fibers" refers to those fibers having a length of at least about 15.9 mm (0.625 inches).

There are a number of manufacturing techniques which may be used to manufacture the topsheet 22. For example, the topsheet may be woven, non-woven, spun-bonded, carded, or the like. A preferred topsheet is carded, and thermally bonded by means well known to those skilled in the fabrics art. Preferably, the topsheet has a weight from about 18 to about 25 grams per square meter, a minimum dry tensile strength of at least about 400 grams per centimeter in the machine direction and a wet tensile strength of at least about 55 grams per centimeter in the cross machine direction.

The absorbent core 26 may be any means which is generally compressible, conformable, non-irritating to the wearer's skin, and capable of absorbing and retaining fluids and certain body exudates. A preferred absorbent core has first and second opposed faces and comprises an absorbent layer 56 and first and second tissue layers 58 and 60, respectively. The first and second tissue layers 58 and 60 overlay the major surfaces of the absorbent layer 56 to form the first and second opposed faces of the absorbent core 26.

The absorbent layer 56 may be manufactured in a wide variety of sizes and shapes (e.g., rectangular, hourglass, etc.) and from a wide variety of liquid absorbent materials commonly used in disposable diapers and other absorbent articles, such as comminuted wood pulp which is generally referred to as airfelt. Examples of other suitable absorbent materials include creped cellulose wadding, absorbent foams, absorbent sponges, super absorbent polymers, or any equivalent material or combination of materials. The total absorbent capacity of the absorbent layer 56 should, however, be compatible with the design exudate loading in the intended use of the diaper 20. Further, the size and absorbent capacity of the absorbent layer 56 may be varied to accommodate wearers ranging from infants through adults.

A preferred embodiment of the diaper 20 shown in FIG. 1 has an hourglass shaped absorbent layer 56 having side edges 62 and end edges 64, and is intended to be worn by infants ranging in weight from about 5 kgs to about 12 kgs (about 12 pounds to about 26 pounds). The airfelt used in absorbent layer 56 weighs from about 30 grams to about 56 grams, has a generally uniform caliper, and has an absorbent capacity of from about 8 grams to about 16 grams of water per gram of absorbent material. It should be understood, however, that the size, shape, configuration, and total absorbent capacity of the absorbent layer 56 may be varied to accommodate wearers ranging from infants through adults.

Therefore, the dimensions, shape, and configuration of the absorbent layer 56 may be varied (e.g. the absorbent layer 56 may have a varying caliper, or a hydrophillic gradient, or may contain superabsorbent materials). Absorbent layer 56 is, therefore, a batt of airfelt about 32 cm wide (lateral dimension), about 45 cm long (longitudinal dimension) and approximately 7 cm across the narrowest part of the crotch portion.

The first and second tissue layers 58 and 60 improve the tensile strength of the absorbent core 26 and reduce the tendency of the absorbent layer 56 to split, lump or ball when wetted. The first and second tissue layers 58 and 60 also help to improve lateral wicking of absorbed exudates, thereby providing a more even distribution of the exudates throughout the absorbent layer 56. While a number of materials and manufacturing techniques may be used to manufacture the first and second tissue layers 58 and 60, satisfactory results have been obtained with sheets of tissue paper having a basis weight of about 16 grams per square meter (10 lbs. per 3000 square feet) and having an air permeability of about 30.5 cubic meters per minute per square meter (100 cubic feet per minute per square foot) at a pressure differential of about 12.8 millimeters of water ($\frac{1}{2}$ inch). While the first and second tissue layers 58 and 60 are preferably coterminous with the absorbent layer 56, they may have different dimensions, a different configuration, or they may be omitted entirely.

The absorbent core 26 is superimposed on the backsheet 24 and is preferably attached thereto by attachments means (not shown) such as those well known in the art. For example, the absorbent core 26 may be secured to the backsheet 24 by a uniform continuous layer of adhesive, a patterned layer of adhesive, or an array of separate lines or spots of adhesive. An adhesive which has been found to be satisfactory is manufactured by Eastman Chemical Products Company of Kingsport, Tenn. and marketed under the tradename Eastobond A-3.

The backsheet 24 is impervious to liquids and is preferably manufactured from a thin plastic film, although other flexible liquid impervious materials may also be used. The backsheet 24 prevents the liquids absorbed and contained in the absorbent core 26 from wetting articles which contact the diaper such as bedsheets and undergarments. Preferably, the backsheet 24 is a polyethylene film having a thickness of from about 0.012 mm (0.5 mil) to about 0.051 cm (2.0 mils), although other flexible, liquid impervious materials may be used. As used herein, the term "flexible" refers to materials which are compliant and which will readily conform to the general shape and contours of the human body.

A suitable polyethylene film is manufactured by Monsanto Chemical Corporation and marketed in the trade as Film No. 8020. The backsheet 24 is preferably embossed and/or matte finished to provide a more clothlike appearance. Further, the backsheet 24 may permit vapors to escape from the absorbent core 26 while still preventing exudates from passing through the backsheet 24.

The size of the backsheet 24 is dictated by the size of the absorbent core 26 and the exact diaper design selected. In a preferred embodiment, the backsheet 24 has a modified hourglass shape extending beyond the absorbent core 26 a minimum distance of at least about 1.3 cm to about 2.5 cm (about 0.5 to about 1.0 inch) around the entire diaper periphery 38.

The topsheet 22 and the backsheet 24 are associated together in any suitable manner. As used herein, the term "associated" encompasses configurations whereby the topsheet 22 is directly joined to the backsheet 24 by affixing the topsheet 22 directly to the backsheet 24, and configurations whereby the topsheet is indirectly joined to the backsheet 24 by affixing the topsheet 22 to intermediate members which in turn are affixed to the backsheet 24. In a preferred embodiment, the topsheet 22 and the backsheet 24 are joined directly to each other in the diaper periphery 38 by attachment means as are known in the art. For example, a uniform continuous layer of adhesive, a patterned layer of adhesive, or an array of separate lines or spots of adhesive may be used.

Tape tab fasteners 28 are typically applied to the waist region 50 of the diaper 20 to provide a fastening means to hold the dipaer on a wearer. Tape tab fasteners 28 can be any of those well known in the art, such as the fastening tape disclosed in U.S. Pat. No. 3,848,594 issued to Buell on Nov. 19, 1974, which is incorporated herein by reference. These fastening tapes, or other diaper fastening means, such as pins, are typically applied near the edge of a diaper in its "in-use" configuration.

Elasticized side flaps 30 are disposed in the diaper 20 adjacent the periphery 38 of the diaper 20 along each longitudinal edge 44 and 46 so that the side flaps 30 tend to draw and hold the diaper 20 against the legs of the wearer. While the elasticized side flaps 30 may be constructed of any of several means as are well known in the diaper art, a particularly preferred construction comprises a flexible side flap 30 and elastic members 32, as is described in detail in the hereinbefore referenced U.S. Pat. No. 3,860,003. In addition, a method and apparatus suitable for manufacturing a disposable diaper having elasticized side flaps are described in U.S. Pat. No. 4,081,301 entitled "Method and Apparatus for Continuously Attaching Discrete, Stretched Elastic Strands to Predetermined Isolated Portions of Disposable Absorbent Articles" which issued to K. B. Buell of Mar. 28, 1978 and which patent is incorporated herein by reference.

The side flaps 30 should be highly flexible and thus contractible so that the elastic member 32 may gather the side flap 30 to provide an elasticized side flap 30 about the body of the wearer. The side flaps 30 are that portion of the diaper 20 between the periphery 38 and the longitudinal edges 62 of the absorbent core 26. Thus in the preferred embodiment of the present invention, the side flaps 30 are formed from the extension of the fluid impervious backsheet 24 and the fluid pervious topsheet 22 outwardly from and along the longitudinal edges 62 of the absorbent core 26 of the diaper 20 in at least the crotch region 54.

The elastic members 32 are secured to the side flaps 30 in an elastically contractible condition so that in a normally unrestrained configuration the elastic members 32 effectively contract or gather the side flaps 30. The elastic members 32 can be secured to the side flaps 30 in an elastically contractible condition in at least two ways. For example, the elastic members 32 may be stretched and secured to the side flaps 30 while the side flaps 30 are in an uncontracted condition. Alternatively, the side flaps 30 can be contracted, for example by pleating, and the elastic members 32 secured to the contracted leg side flaps while the elastic members 32 are in their unrelaxed or unstretched condition.

In the embodiment illustrated in FIG. 1, the elastic members 32 extend essentially the entire length of the side flaps 30 in the crotch region 54 of the diaper 20. Alternatively, the elastic members 32 may extend the entire length of diaper 20, or any other length suitable to provide an elastically contractible side flap 30. The length of the elastic members 32 is dictated by the diaper's design.

In the diaper 20 of FIG. 1, the elastic members 32 are secured to the backsheet 24 with elastic attachment means (not shown). The elastic attachment means herein are preferably hot melt adhesives such as marketed by Findley Adhesives Incorporated, Elm Grove, Wis. as Findley Adhesives 581. A more detailed description of the manner in which elastic strands should be positioned and secured to disposable diapers and briefs can be found in U.S. Pat. No. 4,253,461 issued to Strickland and Visscher on Mar. 3, 1981, and U.S. Pat. No. 4,081,301 issued to Buell, both of which are incorporated herein by reference.

One elastic member 32 which as been found to suitable is an elastic strand having a cross section of 0.18 mm by 1.5 mm and made from natural rubber as available from Easthampton Rubber Thread Company of Stewart, Va., under the trademark L-1900 Rubber Compound. The elastic member 32 may also comprise any heat shrinkable elastic material as is well known in the art. Other suitable elastic members can be made from natural rubber, such as elastic tape sold under the trademark Fulflex 9211 by Fulflex Company of Scotland, N.C. Other suitable elastic members 32 may comprise a wide variety of materials as are well known in the art including elastomeric films, polyurethane films, elastomeric foams, and formed elastic scrim.

In addition, the elastic members 32 may take a multitude of configurations. For example, the width of the elastic members may be varied from about 0.25 mm (0.01 inches) to about 25 mm (1.0 inches) or more; the elastic members 32 may comprise a single strand of elastic material or may comprise several parallel or non-parallel strands of elastic material; or the elastic members may be rectilinear or curvilinear. Still further, the elastic members 32 may be affixed to the diaper in any of several ways which are well known in the art. For example, the elastic members may be ultrasonically bonded or heat sealed into the diaper using a variety of bonding patterns or the elastic members may simply be glued to the diaper 20.

The reservoir 36 is a member in which body exudates are collected, contained and held. The reservoir 36 is preferably a member disposed below the top surface of the diaper 20 so that exudates which float or flow along the top surface will flow into and down the side walls of the reservoir 36 and be collected in the bottom of the reservoir 36 until the diaper can be removed. The reservoir 36 is, therefore, especially effective for exudates, particularly loose fecal materials, that are not easily absorbed by the absorbent core 26 and tend to "float" on the topsheet 22.

The reservoir 36 may be disposed between the elastic members 32 and the longitudinal centerline 51 of the diaper 20. Preferably, the reservoir 36 is disposed between the elastic members 32 and the side edges 62 of the absorbent core 26 in the side flaps 30 so as to provide the maximum amount of containment.

The reservoir 36 may be constructed in a variety of ways using a variety of materials. The reservoir 36 may be constructed of any materials as are known in the art which are compliant and conformable enough to present a pocket or well-like shape. The material may be absorbent, wicking or impermeable to exudates. For example, the reservoir 36 may comprise an element (i.e., the topsheet 22, the backsheet 24 or the side flap 30) or any combination of these elements or other elements of the diaper 20 configured or folded to present a reservoir. In addition, the reservoir 36 may have a variety of shapes and cross-sections provided that a pocket or well-like shape, as shown in FIG. 3, is formed to contain and hold the exudates. For example, the reservoir 36 may have a semi-circular, square or parabolic cross-section.

Preferably, the reservoir 36 is formed by C-folding the side flap 30 and securing a portion of the side flap 30 to portions of the topsheet 22 adjacent portions of the absorbent core 26. As shown in FIG. 3, the reservoir 36 is made of the side flaps 30, the reservoir walls and bottom created by the side flap 30. In this embodiment, the reservoir 36 has a parabolic cross-section.

The securing means 33 for securing length portions of the side flaps 30 to the topsheet 22 are any securement means as are generally well known in the art. For example, the securing means 33 may be ultrasonically bonding or heat/pressure sealing. Preferably, the securing means are a glue spot 34. (A "spot" being defined simply as an area of glue). There may be one or a plurality of glue spots 34 disposed on each side flap 30 for forming the reservoir 36. The glue spots 34 are preferably hot melt adhesives such as marketed by Findley Adhesives Incorporated, Elm Grove, Wis. as Findley Adhesives 581.

The securing means 33 of the present invention are preferably disposed on the side flap 30 prior to the side flap being folded. This location is preferred for ease of application. However, the securing means 33 may alternatively be disposed on the topsheet 22 or both the topsheet and the side flap 30 or in any other area to secure the elements together. In addition, the second fold and the first fold of the C-fold may be secured together by securing means.

Diaper 20, is applied to a wearer, by positioning the waist region 50 under the wearer's back, and drawing the remainder of the diaper 20 between the wearer's leg so that the waist region 48 is positioned across the front of the person. The ends of the tape-tab fasteners 28 are then secured to outwardly facing areas of the diaper 20. In this manner, the reservoirs 36 should be disposed in the crotch region of the wearer and should provide the dispositions and funtions described hereinbefore. The elasticized side flaps 30 encircle the thighs and create a gasketing barrier against the thighs.

Basically, without intending to limit the present invention, the present invention is a diaper that is especially useful and leakage resistant against loose fecal material, the improved containment characteristics being achieved in the following manner. As loose fecal material is discharged onto the topsheet 22, the material flows or floats on the top surface of the topsheet 22. (Hereinafter referred to as surface material). The surface material moves from the point of discharge toward the longitudinal edges 44 and 46 of the diaper 20. Surface material will flow into the reservoir 36 at the opening. In normal use, gravitational forces will tend to cause the surface material to collect in the reservoir 36. Improved containment is achieved because surface material would have to flow up the reservoir 36, which direction is substantially directly against the force of gravity when the wearer is in an upright position, in order to penetrate and flow over the reservoir 36. However, should such material flow out of or beyond the reservoir 36, it is retarded from leaking out of the diaper 20 by the gasketing effect achieved by the elasticized side flaps 30, as they draw and gather about the legs of the wearer, thereby providing a second and independent effective barrier against leakage so as to further prevent the soiling of adjacent garments.

In addition, the diaper 20 achieves increased comfort in the following manner. Because the diaper 20 is folded along the side flaps 30, the elastic members 32 and hence the elasticized side flaps are positioned closer to the side edge 62 of the absorbent core 26. Thus, when initially placed on the wearer, the elasticized side flaps ride in the groin areas along the inner thighs of the wearer thereby providing a better initial fit. This positioning provides a better initial fit on the wearer because elasticized side flaps of conventional diapers are initially positioned to ride farther down on the thigh of the wearer. The elasticized side flaps subsequently tend to ride or creep up into the groin regions of the wearer during use. Because the side flaps are drawn up, gaps tend to form in the legs and waist providing less comfort for the wearer. However, because the present invention initially positions the elasticized side flaps in the groin areas, sagging of the diaper is reduced resulting in increased comfort for the wearer.

Figure 4:
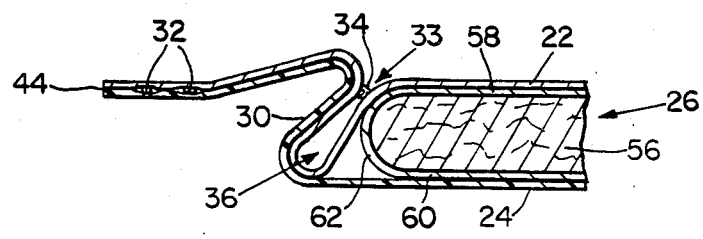
FIG. 4 is a fragmentary sectional view of an alternative embodiment of the present invention.

FIG. 4 is a fragmentary sectional view of an alternative embodiment of the diaper 20 of the present invention. The reservoir 36 is formed by securing portions of the side flap 30 to the topsheet 22 adjacent the side edge 62 of the absorbent core 26. The reservoir is shown as closed in this view by the securing means 33 such as glue spot 34.

Figure 5:
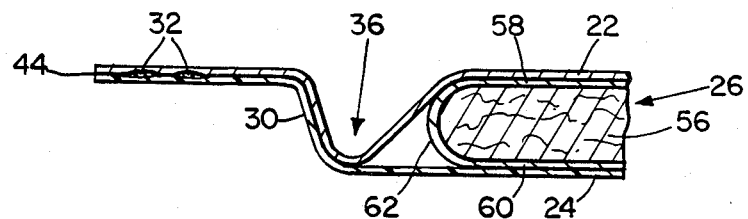
FIG. 5 is another fragmentary sectional view of the alternative embodiment of the present invention shown in FIG. 4.

FIG. 5 is a fragmentary sectional view of the alternative embodiment of the present invention shown in FIG. 4. The reservoir is shown as standing open ((i.e., ready to collect, contain and hold unabsorbent exudates).

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article having a front waist region, a crotch region and a back waist region, said absorbent article comprising:
   a liquid pervious topsheet;
   a liquid impervious backsheet associated with said topsheet;
   an absorbent core having side edges, said absorbent core disposed between said topsheet and said backsheet;
   a flexible side flap extending outwardly from and along each side edge of said absorbent core in at least the crotch region;
   an elastic member secured to each of said side flaps;
   a securing means for securing portions of said side flaps to said topsheet; and
   a reservoir formed by a portion of each of said side flaps arranged in a multiplicity of layers, a first layer being formed by an inwardly longitudinally extending fold in said side flap and a second layer formed by an outwardly longitudinally extending fold, a portion of said first layer being secured to said topsheet by said securing means, the remaining portions of said first fold being unsecured, and a portion of said second layer being secured to a portion of said first layer.

2. The disposable absorbent article of claim 1 wherein said securing means is a glue spot.

3. The disposable absorbent article of claim 1 wherein said securing means is a pressure and heat bonded pattern.

4. A disposable absorbent article having a front waist region, a crotch region and a back waist region, said absorbent article comprising:
   a liquid pervious topsheet;
   a liquid impervious backsheet associated with said topsheet;
   an absorbent core having said edges, said absorbent core disposed between said topsheet and said backsheet;
   a flexible side flap extending outwardly from and along each side edge of said absorbent core in at least the crotch region;
   an elastic member secured to each of said side flaps;
   a securing means for securing portions of said side flap to said topsheet; and
   a reservoir formed by a portion of said side flap being secured to said topsheet adjacent said side edge of said absorbent core by said securing means, the remaining portions of said side flaps being unsecured.

5. The disposable absorbent article of claim 4 wherein said securing means is a glue spot.

* * * * *

UNITED STATES PATENT AND TRADEMARK OFFICE
CERTIFICATE OF CORRECTION

PATENT NO.   :   4,681,579

DATED        :   July 21, 1987

INVENTOR(S)  :   JOHN W. TOUSSANT, et al.

It is certified that error appears in the above-identified patent and that said Letters Patent is hereby corrected as shown below:

Column 1, Line 15,      "ae" should read ---are---.

Column 1, Line 32,      "elasticizied" should read ---elasticized---.

Column 3, Line 5,       before "securing" insert ---and---.

Column 3, Line 19,      "dimension" should read ---dimensions---.

Column 3, Line 33,      before "is" insert ---encircle the waist of the wearer. The crotch region 54 is that portion of the diaper 20 between the waist regions 48 and 50, and comprises that portion of the diaper 20 which, when worn,---.

Column 6, Line 23,      before "edge" insert ---top---.

Column 7, Line 21,      "as" should read ---has---, and before "suit" insert ---be---.

Signed and Sealed this

Seventeenth Day of November, 1987

Attest:

DONALD J. QUIGG

Attesting Officer          Commissioner of Patents and Trademarks